(12) United States Patent
Goldberg et al.

(10) Patent No.: US 9,078,932 B2
(45) Date of Patent: Jul. 14, 2015

(54) MAGNETIC CELLS FOR LOCALIZING DELIVERY AND TISSUE REPAIR

(75) Inventors: Jeffrey L. Goldberg, Coral Gables, FL (US); Alan Halpern, Kalamazoo, MI (US)

(73) Assignee: EMMETROPE, INC., Key Biscayne, FL (US)

( * ) Notice: Subject to any disclaimer, the term of this patent is extended or adjusted under 35 U.S.C. 154(b) by 284 days.

(21) Appl. No.: 12/866,004

(22) PCT Filed: Feb. 4, 2009

(86) PCT No.: PCT/US2009/033086
§ 371 (c)(1),
(2), (4) Date: Aug. 3, 2010

(87) PCT Pub. No.: WO2009/100137
PCT Pub. Date: Aug. 13, 2009

(65) Prior Publication Data
US 2011/0003003 A1 Jan. 6, 2011

Related U.S. Application Data

(60) Provisional application No. 61/006,861, filed on Feb. 4, 2008.

(51) Int. Cl.
*A61K 47/48* (2006.01)
*A61N 2/00* (2006.01)
*A61K 9/50* (2006.01)
A61K 35/12 (2015.01)
A61K 35/44 (2015.01)
A61K 41/00 (2006.01)
C12N 5/00 (2006.01)
A61K 9/00 (2006.01)
A61K 9/51 (2006.01)

(52) U.S. Cl.
CPC ......... *A61K 47/48776* (2013.01); *A61K 9/5094* (2013.01); *A61K 47/48884* (2013.01); *A61N 2/002* (2013.01); *A61K 9/0034* (2013.01); *A61K 9/5115* (2013.01); *A61K 35/12* (2013.01); *A61K 35/44* (2013.01); *A61K 41/00* (2013.01); *C12N 5/0006* (2013.01)

(58) Field of Classification Search
CPC .......... A61K 47/48776; A61K 9/5094; A61N 2/0002
See application file for complete search history.

(56) References Cited

U.S. PATENT DOCUMENTS

| | | | |
|---|---|---|---|
| 4,206,094 A | 6/1980 | Molday et al. | |
| 6,203,487 B1 | 3/2001 | Consigny | |
| 6,551,843 B1* | 4/2003 | Rao et al. | 436/526 |
| 2006/0264690 A1 | 11/2006 | Ochi | |
| 2008/0019917 A1* | 1/2008 | Pacey | 424/9.3 |

FOREIGN PATENT DOCUMENTS

| | | | |
|---|---|---|---|
| WO | WO 01/81551 A2 * | 11/2001 | C12N 5/06 |
| WO | 04/000369 A2 | 12/2003 | |
| WO | 2005/059118 A2 | 6/2005 | |

OTHER PUBLICATIONS

Gould and Auchincloss. Immunology Today 20(2):77-82, 1999.*
Azimzadeh et al. Hematology and Cell Therapy 38(4):331-343, 1997.*
Sylvester et al. Arch Surg. 139:93-99, 2004.*
Sawant R.M. et al, "SMART drug delivery systems: double targeted pH-responsive pharmaceutical nanocarriers", Bioconjug. Chem., 2006, vol. 17, No. 4, pp. 943-949.
Haruta, M., "Embryonic stem cells: potential source for ocular repair", Semin. Ophthalmol., 2005, vol. 20, No. 1, pp. 17-23 (Abstract).
Ingrid Hilger et al., "Magnetic nanoparticles for selective heating of magnetically labelled cells in culture: preliminary investigation; Magnetic nanoparticles for selective heating of magnetically labelled cells in culture: preliminary investigation", Nanotechnology, IOP, Bristol, GB vol. 15, No. 8 Aug. 1, 2004, pp. 1027-1032: ISSN: 0957-4484.
Supplemental European Search Report dated Aug. 21, 2014.
Cartmell S H et al., "Use of magnetic particles to apply mechanical forces for bone tissue engineering purposes", Journal of Physics: Conference Series, Institute of Physics Publishing. Bristol, GB, vol. 17, No. 1 Jan. 1, 2005, pp. 77-80.

* cited by examiner

*Primary Examiner* — Marcia S Noble
(74) *Attorney, Agent, or Firm* — Kacvinsky Daisak Bluni PLLC

(57) ABSTRACT

Normal or genetically modified cell(s) having magnetic nanoparticle(s) bound (affixed) to their surfaces and methods of delivery to target tissues, e.g. for treatment of disease and or injury.

15 Claims, 2 Drawing Sheets

MAGNETIC CELLS FOR LOCALIZING DELIVERY AND TISSUE REPAIR

RELATED APPLICATIONS

This application is a national stage application under 35 U.S.C. 371 of International Application PCT/US2009/033086 filed Feb. 4, 2009, which claims priority from U.S. provisional application 61/006,861 filed Feb. 4, 2008, all of which are incorporated by reference in their entireties herein.

The invention described herein was developed in part using funds from a grant from the Government of the United States of America (NEI/NIH grant no. R21-017971). The United States Government has certain rights in the invention.

FIELD OF THE INVENTION

The invention relates to magnetic cell(s), and methods of use. The cells are either naturally occurring or genetically altered animal somatic or stem cell(s), generated either from a patient/individual or from a living or deceased donor. Magnetic particles are affixed to the outer surface of the cell. The magnetic cell(s) can then be administered to a subject, e.g. by injection or implantation, and their localization controlled by application of an external magnetic field, e.g. a magnet positioned outside the body. This allows the cells to be magnetically directed to specific sites in the body, wherein the cells themselves, or various contents thereof such as enzymes, hormones, transmitters, and the like, will be useful for investigational, diagnostic or therapeutic purposes.

BACKGROUND

A large number of diseases and disorders result, from the dysfunction of a specific tissue or organ. A number of these are currently treated by transplantation, e.g. heart transplantation for certain types of cardiac dysfunction, corneal transplantation for endothelial cell dysfunction, stem cells for retinal neuroprotection, etc. However, transplantation procedures are invasive, have varying rates of success, and are not yet even available for many types of diseases or disorders, in particular for a number of eye diseases, for example, including diseases of the cornea (including but not limited to endothelial or stromal dystrophies), diseases of retinal ganglion cells and the optic nerve (including but not limited to glaucoma, ischemic optic neuropathies, other optic neuropathies), and diseases of retinal photoreceptors and retinal pigment epithelium (including but not limited to Leber's congenital amaurosis, retinitis pigmentosa and age-related macular degeneration)

Although in many cases it would seem desirable to administer new "healthy" cells, e.g. by injection or infusion, simply injecting such cells generally does not work as they do not remain localized and stick to or become incorporated into the patients' tissue. For example, healthy corneal endothelial cells are inefficiently incorporated into a patient's diseased cornea when injected into the anterior chamber of the eye (e.g. Mimura et al, Invest. Oplrthalmol. Vis. Sci. 2005, 46(10):3637-44), and healthy retinal ganglion cells are not incorporated into the retina when injected into the vitreous cavity of the eye. Most current technology depends on whole tissue transplants, or in the case of stem cell clinical trials, there are no techniques for controlling the cells' localization in vivo. A stem cell transplantation clinical trial for retinitis pigmentosa, for example, uses subretinal injection of hematopoetic stem cells, but does nothing to control their localization there, or keep them from floating or migrating away after surgical implantation. As another example, corneal endothelial cells injected into the anterior chamber of the eye will simply fall by gravity away from the cornea, and not properly attach. Thus, there remains a need for new methods for targeting cells to specific tissues for therapeutic purposes.

Consigny (U.S. Pat. No. 6,203,487) described a method in which magnetic particles of micron size are inserted into cells for the purpose of focalized delivery. In the present application, a method of attaching magnetic nanoparticles with diameters of 500 nm or less to the outer surface of cells and delivering them to a target tissue is described. This is advantageous in many applications (e.g. applications involving the eye), because smaller particles that are not internalized into cells can be degraded from the cell surface and easily excreted after the cells have been situated. For example, in applications involving the eye, the particles can be excreted without clogging ocular outflow and thereby raising intraocular pressure.

SUMMARY

It is an object to provide a method for delivery of specific cells to a target tissue of a subject by attaching or affixing magnetic particles to the outer surface of said cells, administering the magnetic particle-comprising cell to the subject, and applying a magnetic field to said target tissue under conditions such that said magnetic particle-comprising cell is delivered to the target tissue. The coated particles and cells comprising them are useful, for example, for prevention or treatment of diseases and disorders.

Accordingly, the invention provides magnetized cells comprising coated magnetic nanoparticles, methods of obtaining the magnetized cells, methods of delivering them to target tissues, and methods of prophylaxis and/or treatment of diseases and disorders using the magnetized cells.

Specific cells for magnetization by attachment of particles and delivery include, e.g., neurons, neuroglial cells, endothelial cells, fibroblasts, smooth or skeletal muscle cells, epithelial cells, pancreatic islet cells, hepatocytes, schwann cells, dermal cells, kidney cells, bladder cells, cartilage cells, or bone cells. For example, relevant to the eye and visual system, ocular cells, optic nerve cells, corneal cells, whether epithelial, stromal, or endothelial; a retinal cell, whether a retinal neuron such as a retinal ganglion cell or photoreceptor or other retinal neuron, or a retinal glial cell whether a retinal muller glial cell or retinal astrocyte or other, or a retinal endothelial cell or pericyte; a retinal progenitor cell; a retinal stem cell; an optic nerve glial cell whether an astrocyte, oligodendrocyte, microglial cell, or one of their precursors; or another stem or progenitor cell capable of either differentiating into an ocular or optic nerve cell or capable of supporting the survival or growth or normal function of an ocular or optic nerve cell are delivered to specific areas of the eye. Cells may be normal or genetically modified, e.g. by insertion of particular gene(s) or gene fragments that may be considered advantageous for the condition being treated. For specific applications, at least one, but typically many nanoparticles will be affixed or bound to an individual cell.

The term "subject" is intended to mean an animal, for example a mammal, in particular a human.

The term "magnetic nanoparticle" is intended to mean a particle of no larger than about 500 nm, more usually no larger than 200 nm, having magnetic properties. Particles that can be used include nanospheres, conjugates, micelles, colloids, aggregates and complexes comprising ferromagnetic, paramagnetic or superparamagnetic material, such as iron, nickel, cobalt, and alloys thereof, as suitable for in vivo use. For example, the magnetic nanoparticles may comprise iron in any ferromagnetic form, with or without an inert surface coating, with its surface chemically modified to allow the binding of an antibody, or antibody fragment, or protein or sugar fragment that binds to cells. Persons of skill in the art will appreciate that compounds having excessive toxicity when used according to the method are to be avoided. It is expected that in many applications the particles will be absorbed and excreted over time, and that small amounts of otherwise toxic particles may accordingly not present a problem when used in the method.

In general, it is expected that the magnetic nanoparticles will have a mean diameter of between 5 and 500 nm, more particularly between 40 and 400 nm, most particularly between 40 and 100 nm, with a standard deviation of 50% or lower, more usually 20% or lower. Difficulties in using nanoparticles over micron-scale particles include particle aggregation, particle tracking and observation, and ability to mobilize the particles by external magnetic fields, all of which are considerably easier when using micron-scale or larger particles. For this reason, previous efforts likely focused on micron-scale particles and ignored the possible advantages of nanoparticles. We have overcome a number of these difficulties, and have now discovered a number of advantages of using nanoparticles over micron-scale particles. Advantages include ability to bind to cell surfaces without stimulating endocytosis; ability to be shed from cell surfaces or, when internalized, excreted from cells; and ability to be excreted from the eye or the body when shed from cells.

Coatings to be affixed to the particles include non-specific binding agents such as inert metals like gold or dextrans or polymers; and/or specific binding agents such as antibodies that are specific to cell-surface antigens. For example, antibodies directed against SSEA-1 bind to many types of stem cells, and nanoparticles coated with anti-SSEA-1 antibodies can be used to convert stem cells into magnetic stem cells. Similarly, many cells express specific integrin receptors, and antibodies against these integrin receptors bound to magnetic nanoparticles bind to specific cells such as corneal endothelial cells and create magnetic corneal endothelial cells.

Coatings are affixed to the particles by standard methods used broadly in the field (for example, see (Schroder et al., 1986; Douglas et al., 1987; Sestier et al., 1998; Perrin et al., 1999; McCloskey et al., 2000; Tibbe et al., 2001).

By "target tissue" is meant any specific tissue type or location, e.g. within an organ or tissue, to which it is desirable to deliver the cells. For example, ocular cells or other stem cells may be delivered to the eye, or a specific region of the eye, e.g. to the cornea, optic nerve, retina, etc.

The magnetic nanoparticles can be affixed to the surface of the cells by any effective means known to those of skill in the art. For example, the magnetic particle may be affixed to the cell by means of an antibody, e.g. an antibody specific for a surface antigen present on the cell. Surface coatings comprising, for example, anti-L1, anti-trkB, anti-integrin, and cholera toxin subunit B may be placed on the magnetic particles for the purpose of attaching them to retinal ganglion cells. The magnetic particle may also be affixed to the cell using a specific ligand for which a receptor is present on the cell. For example, the magnetic particles can be functionalized for attachment to retinal ganglion cells (RGCs) using brain-derived neurotrophic factor (BDNF). Other means of attaching the particles to the cells include non-specific chemical modifications such as carboxy or amide groups, or coatings of sugars or dextrans, or coatings of polymers such as amino acids polymers like poly-lysine, or coatings of otherwise inert coatings that bind cells. Coated magnetic nanoparticles will be affixed to the outer surface of cells by co-incubation in a general media that affords adequate cell survival during the co-incubation period; the media is not generally found to be germane to the affixing process. In general, a balanced salt solution at physiologic pH around 7.4 will suffice; supplements to the media that enhance cell survival during the process are the topic of other published work specific to cell types being used and are not germane to this invention. Co-incubation time and temperature may depend on the specific cell type being converted into a magnetic cell; for example, binding to retinal ganglion cells using magnetic nanoparticles coated with an anti-TrkB antibody occurs maximally after 4 hours at 37 degrees celcius, but may also be performed by co-incubation at 4° C. overnight. Excess magnetic nanoparticles not bound to cells can be washed away either by spinning the cells down in a centrifuge at a speed that pellets the cells but not the unbound magnetic nanoparticles, or by eluting the magnetic nanoparticle-bound cells away from the unbound cells using a magnetic field, or both.

The magnetic nanoparticle comprising cells may be administered to a subject by any suitable means, e.g. by injection, infusion or surface application. The cells may be suspended in any pharmaceutically/physiologically acceptable medium or solution, such as for example, isotonic saline solution or culture medium suitable for in vivo delivery to a subject. Additional excipients and carriers may be added as are found suitable by those of skill in the art. Suitable solutions and delivery vehicles are described in Remington: The Science and Practice of Pharmacy, $21^{st}$ Ed. (2005). For some applications, such as delivery of replacement cells to the corneal endothelium for endothelial damage or dystrophy, or delivery of stem cells under the retina for age-related macular degeneration or retinitis pigmentosa, $10^3$-$10^6$ cells will be delivered by injection in a volume of 3-300 µL but more typically around $10^4$ cells in a volume of 10-100 µL. In other applications, such as delivery of stem cells to enhance retinal ganglion cell survival in diseases like glaucoma or ischemic optic neuropathy, $10^3$-$10^6$ cells will be delivered by injection in a volume of 3-300 µL but more typically around $10^5$ cells in a volume of 200 µL. In other applications, such as delivery of replacement liver cells in diseases like cirrhosis or hepatitis, $10^6$-$10^9$ cells will be delivered by intravenous infusion in a volume of 1-500 mL but more typically around $10^7$ cells in a volume of 200 mL. When considering the delivery of cells meant for carrying toxic compounds to specific tissues for example in cancer therapeutics, the cell number will have to be carefully titrated against systemic toxicity to the patient.

Also provided are normal or genetically modified cell(s) having a magnetic nanoparticle bound or affixed to its surface covalently or by antibody-antigen linkage, in particular ocular cells such as corneal cell(s), whether epithelial, stromal, or endothelial; retinal cell(s), whether a retinal neuron such as a retinal ganglion cell or photoreceptor or other retinal neuron, or retinal glial cell(s) whether retinal muller glial cell(s) or retinal astrocyte(s) or other, or retinal endothelial cell(s) or pericyte(s); retinal progenitor cell(s); retinal stem cell(s); optic nerve glial cell(s) whether an astrocyte(s), oligodendrocyte(s), microglial cell(s), or their precursors; or other stem or progenitor cell(s) capable of either differentiating into ocular or optic nerve cell(s) or supporting the survival or growth or normal function of an ocular or optic nerve cell. In one embodiment, the magnetic particle(s) are bound via an antibody-antigen complex. In general, the magnetic particle will have a diameter of less than 500 nm, preferably less than 200 nm, more preferably less than 100 nm. The magnetic particle may comprise iron in any ferromagnetic form, with or without an inert surface coating, with its surface chemically modified to allow the binding of an antibody, or antibody fragment, or protein or sugar fragment that binds to cells. The particle may also comprise other magnetic substances, such as nickel or cobalt.

Typically, the magnetic particle-comprising cells will be isolated cells, that is, contained/maintained in an environment that is distinct from their natural state. For example, the cells may be grown in tissue culture, or isolated from a donor animal or a subject who is to be treated, and maintained under suitable in vitro conditions for modification and use.

Cells with magnetic nanoparticles so bound can be used to treat a variety of diseases and disorders of the eye, such as, for example, macular degeneration, retinitis pigmentosa, and other retinal degenerations; glaucoma, ischemic optic neuropathy, and other retinal ganglion cell and optic nerve degenerations; Fuch's endothelial dystrophy, pseudophakic bullous kerathopathy, and other corneal endothelial cell degenerations; corneal epithelial cell degeneration, corneal limbal cell deficiency, and other corneal epithelial cell degenerations; ocular melanoma, lymphoma, and other ocular cancers. The cells comprising magnetic nanoparticles can also be used to treat other diseases and disorders wherein it may be desirable or advantageous to target a specific tissue with cells so modified. See, for example, Consigny, U.S. Pat. No. 6,203,487.

The type of cells to be magnetized and delivered will depend upon the specific condition to be treated, e.g. for repair or therapy of tissues other than eye, stem cells capable of differentiation into the desired tissue type, e.g. muscle, skin, nerve, etc., could be delivered. For example, photoreceptor or stem cells can be delivered to the macula for treatment of Retinitis pigmentosa; endothelial cells or stem cells can be delivered to cornea for treatment of Fuch's endothelial dystrophy or Pseudophakic bullous keratopathy; stem cells can be delivered to cornea for treatment of Corneal epithelial disturbance including limbal stem cell deficiency; retinal ganglion cells can be delivered to retina and optic nerve for treatment of glaucoma or Ischemic optic neuropathy; ocular melanoma could be treated by delivery of a toxin-expressing cell type to the melanoma; Cirrhosis could be treated by delivery of hepatocytes to the liver; heart failure could be treated by delivery of cardiac myocytes to the heart; adenocarcinoma, carcinoma, or lymphoma could be treated by delivery of toxin-containing cells to the malignant tumor; skin wounds could be treated by delivery of fibroblasts and epithelial cells to the skin; stroke could be treated by delivery of stem cells to the brain; and spinal cord injury could be treated by delivery of stem cells, neurons, or immune cells to the spinal cord.

The methods and compositions disclosed herein can be used to target stem cells, precursor cells, or mature tissue-specific cells, to any site in the body to facilitate enhanced survival or tissue repair of damaged or diseased tissues. For example corneas are transplanted for endothelial cell dysfunction; this would provide a technique for replacing endothelial cells without the necessity of a whole transplant operation. The present methods can replace whole tissue transplants, or supplement current stem cell technologies.

This application claims priority to U.S. provisional application No. 61/006,861, filed Feb. 4, 2008, which is incorporated herein by reference in its entirety.

DETAILED DESCRIPTION

General Methods

Cells

Cells for magnetization and use in the method can be obtained according to known protocols. For examples below, RGCs were purified to homogeneity (>99.5%), separating them from all other retinal neurons as well as all other CNS glial cells (Meyer-Franke et al., 1995; Goldberg et al., 2002b; Goldberg et al., 2002a). Purification of RGCs will allow more rapid identification of nanoparticle binding and endocytosis, and will allow us to better characterize the force versus axon growth rate. In other examples, CNS glia, both astrocytes and oligodendrocytes (Goldberg et al., 2002b; Goldberg et al., 2002a) can be purified for testing (Goldberg et al., 2002b; Goldberg et al., 2002a).

Magnetic Nanoparticles

Magnetic nanoparticles in various forms are already in use clinically and in research applications without any demonstrated toxicity. For example, superparamagnetic particles containing monocrystalline iron oxide nanoparticles (MION) of diameters <50 nm have been used as MRI contrast agents. These particles have demonstrated neurologic non-toxicity and axonal transport of ferrous-based agents (Neuwelt et al., 1994). Published studies supporting the use of the MRI contrast agent Ferridex (Advanced Magnetics and Berlex Laboratories) have found no deleterious effects. Furthermore, magnetically directed drug delivery, using tagged pharmaceuticals in the form of magnetic microspheres and magnetic polymer carriers, has shown success in delivering anti-neoplastic drugs and radio-isotopes to magnetically targeted areas in vivo (Schutt et al., 1997; Lubbe et al., 2001).

Coatings

Means for applying the contemplated coatings to magnetic nanoparticles are well known to those of skill in the art. Commercial kits are available having the necessary agents and instructions, for example, as detailed in the description above and examples below (see, e.g., Example 1).

Magnets

Magnets for use in the medical arts and in particular for localizing magnetic particles in tissue are familiar to those of skill in the art. Suitable magnets are described, for example in Consigny (U.S. Pat. No. 6,203,487). The clinical device will include either a superconducting magnet or fixed/rare earth magnet with sufficient field density uniformity and magnetic field gradient to direct the cells and hold them in place. Specifics of magnetic field strength will vary by need, such that stronger fields/gradients will be used when the magnet is required to act at greater distances, and weaker fields/gradients may be used when the magnet can be localized closer to the implanted particles and/or target tissues. We anticipate directing the cells to the target tissue and then modulating the underlying field to further refine their movement and shape the tissue.

EXAMPLES

Example 1

Coating Magnetic Nanoparticles for Surface Attachment

Figure 1A:
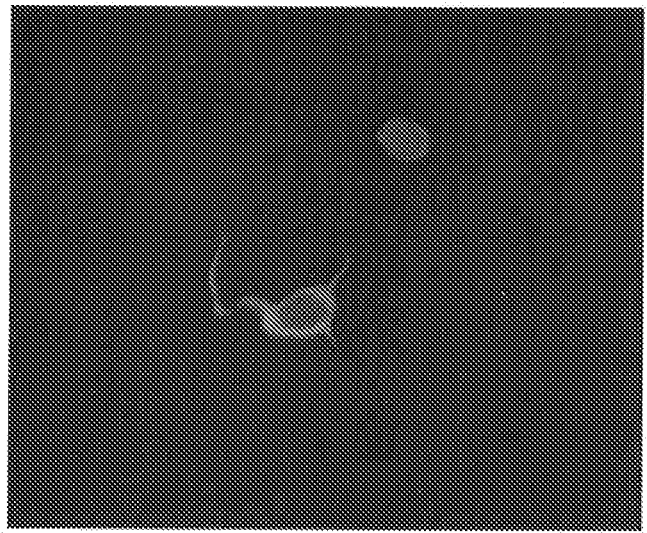
FIG. 1: RGCs express trkB. (A) RGCs immunolabeled with anti-trkB (red; DAPI nuclear counterstaining is blue). (B) RGCs were cultured in growth media including BDNF, CNTF, insulin and forskolin for 24 hours. 1 µm magnetic nanoparticles coated with anti-trkB were subsequently added to the medium for 2 hours, after which time the cultures were washed with fresh medium and the RGCs examined with DIC microscopy.
Figure 1B:
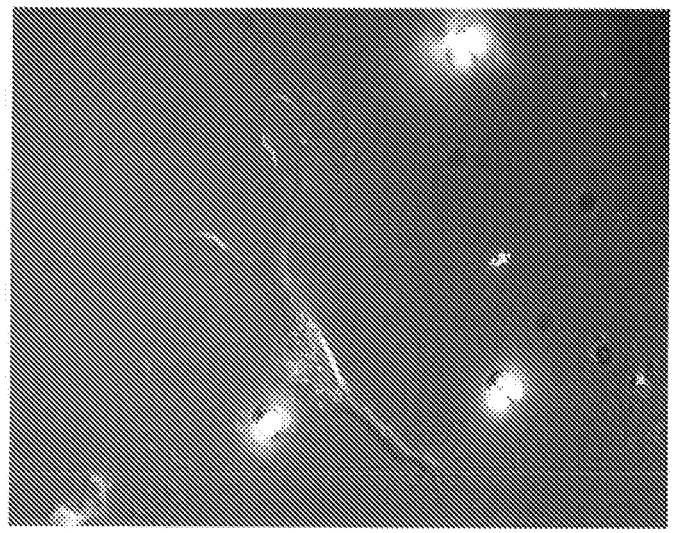

For coating various magnetic nanoparticles for surface attachment to neurons, a procedure analogous to that effective for coating 1 µm particles activated with carboxylic acid (Dynal Biotech, Oslo, NORWAY) or for coating 50 nm particles (e.g. Miltenyi Biotech) with anti-TrkB (BD Bioscience, San Jose, Calif., USA) can be used. The coating procedure is performed according to the manufacturer's standard protocols. Briefly, particles are washed twice with 25 mM MES at approximate pH6 buffer for approximately 10 min each time. Approximately 150 µg of anti trkB in MES buffer is used for functionalizing particles, and slow tilt rotated for approximately 30 min. Then, 0.3 mg of EDC in MES buffer is added, and incubated overnight at 4° C. with tilt rotation. Finally, particles are washed in PBS for four times and PBS is added to a final 1 mg/ml. We found that 1 µm magnetic particles coated in this manner can strongly bind to RGCs (FIG. 1). It is expected that this and similar protocols can be used to coat magnetic nanoparticles down to 25 nm diameter and smaller.

Example 2

Optimal Functionalization (Surface Coating) of Commercially Available Superparamagnetic Nanoparticles to Maximize Binding to Retinal Ganglion Cells Commercially available surface activated superparamagnetic nanoparticles as small as 25 nm (MicroMod Partikeltechnologie GmbH, GERMANY) can be coated according to manufacturers' protocols with functional molecules selected for their ability to strongly and specifically bind neurons. Briefly, tosyl-activated or carboxyl-activated magnetic nanoparticles can be used for attaching antibodies, proteins and other biomolecules that contain primary amino or sulphydryl groups. We will use manufacturers' suggested protocols for nanoparticle and protein/antibody concentrations as a starting point to covalently attach the following proteins: antibodies to the trkB receptor, antibodies to the surface adhesion molecule L1, antibodies to surface integrin receptors, and cholera toxin subunit B, which binds to the GM1 ganglioside on the surfaces of RGCs and other neurons. We have already successfully shown that we can functionalize magnetic nanoparticles using these techniques (see above). The coupling of the functional group will be verified by staining the nanoparticles with fluorescently tagged secondary antibodies directed against the primary antibody/protein. Non-functionalized magnetic nanoparticles will be used as controls. We will confirm that the coating process did not disrupt the ability of these antibodies/molecules to bind their targets.

Example 3

Measurement of Binding Specificity of Magnetic Nanoparticles in Purified and Mixed Cultures To assay for nanoparticle binding by neurons, retinal ganglion cells (RGCs) can be cultured according to standard protocols (Meyer-Franke et al., 1995; Goldberg et al., 2002b). We will add functionalized nanoparticles generated as described above to the RGCs 2 hours after plating, leave them for an additional 1 hour at 37° C., and then exchange the media to remove excess unbound nanoparticles. We will leave the neurons in culture for 1 hour to 3 days, to examine whether the nanoparticles remain attached with time. At the end of the culture period we will use three techniques to confirm nanoparticle binding: (1) direct visualization using high-magnification microscopy available in the lab; (2) commercially available iron staining kits (Sigma) in the case of nanoparticles with exposed iron surfaces; and (3) standard immunohistochemistry with fluorescent secondary antibodies directed against the antibodies/proteins coating the nanoparticles. Using these 3 techniques we will estimate at a gross level the amount of nanoparticle binding by counting nanoparticles or comparing stained cells.

To assay for neuron-specific binding, we will use mixed retinal and cortical cell cultures, both of which we are currently using in the lab. Although most of the studies for initial simplicity will focus on the use of RGCs, we wish to generate at a minimum some indication that the data generated for RGCs will be testable more broadly on other CNS neurons. Approximately 2 hours after plating we will add functionalized magnetic nanoparticles, as above, and exchange the media after 1 hour at 37° C. to remove excess unbound nanoparticles. After 1 hour to 3 days, we will do double immunohistochemistry to determining binding specificity, using antibodies against the neuron-specific surface molecule thy-1 to identify RGCs or cortical neurons.

Example 4

Measurement of Binding Strength in Varying Magnetic Fields

Figure 2:
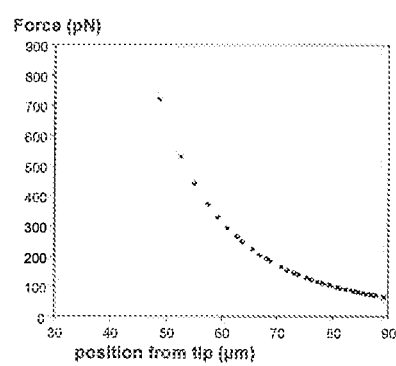
FIG. 2: A force-distance relationship was constructed based on Stokes' law $F=6\pi\eta Rv$, where F is the force due to friction acting on a particle of radius R at a distance d from the tip of the pole piece, traveling at velocity v through a fluid viscosity of µ.

The magnet will first be calibrated to the magnetic nanoparticles to be used, as nanoparticles in different regions in the dish will experience different forces. We will initially calibrate two different magnets: (1) a calibrated permanent magnet, and (2) a sharpened magnetized tip. We will use uncoated magnetic nanoparticles for calibration by suspending them in a high viscosity polydimethylsiloxane solution (PDMS, Sigma). We will use 12,000 centistoke PDMS for 1 µm nanoparticles, and 1,000 centistoke PDMS solution for nanoparticles smaller than 1 µm. We will place the permanent magnet in the middle of a 35 mm Petri dish with glass bottom containing magnetic nanoparticles and PDMS solution. The movement of the nanoparticles towards the magnet will be digitally recorded using videomicroscopy, from which we will calculate position versus time (velocity) of the nanoparticles. We will then plot velocity versus position from magnet to fit a curve, which can then be used to estimate the force versus position (distance) curves based on Stokes' law:

$$F = 6\pi\eta Rv$$

wherein F is the force due to friction, $\eta$ is the fluid viscosity, R is the nanoparticle radius, and v is the nanoparticle velocity. This will give us the force-distance relationship for the specific magnet/nanoparticle in use (see, e.g. FIG. 2).

To measure binding strength of magnetic nanoparticles to neurons, we will add functionalized nanoparticles to the RGC cultures as described above. We will use a calibrated permanent magnet to apply a known force to RGC-nanoparticle pairs. We will note whether the nanoparticle was attached to an axon or the cell body, as binding strength may vary according to the cellular site of attachment. By varying the distance between the nanoparticle and the magnet, we can vary the applied force, for example to increase the force until the nanoparticles detach from the neurons. We will record the time, t, since application of force and the force at which the nanoparticle detaches from the cell/axon. We will use this data for statistical analysis of the binding force of the nanoparticle to a cell for a variety of nanoparticle sizes coated with one of the above mentioned molecules.

Using this technique, we have demonstrated that surface activated nanoparticles can be strongly and specifically attached to neurons and other cells. Optimal nanoparticle size should be able to be determined through routine experimentation. Likewise, antibody and protein coatings can be optimized for individual applications.

Example 5

Delivery of Magnetic Particle-Comprising Cells to a Target Tissue

Magnetic particle-comprising cells as described above can be administered to the subject by any suitable means known in the art, for example, by injection (local or systemic), topical application, infusion, etc. It is expected that for applications involving the eye, topical application or local injection will be preferred. Following administration of the cells, one or more magnets will be positioned so as to cause the cells to migrate to or remain in or at the desired target tissue. The required strength of the magnet and time period necessary for the magnetic force to be applied in order to effect the desired outcome (in most instances, cells being fixed in or attached to the target tissue) can be determined by routine experimentation.

Three such examples are offered in detail.

(a) Delivery of donor or autologous corneal endothelial cells to the corneal endothelial surface of the patient with inadequately functioning endothelium, as in Fuch's Endothelial Dystrophy or Pseudophakic Bullous Keratopathy. Corneal endothelial cells would be isolated from human donor corneas (Joyce et al., 1990; Joyce et al., 1996; Chen et al., 2001; Joyce, 2003; Joyce and Zhu, 2004; Zhu and Joyce, 2004) or derived from human stem cells in cultures by other technologies (Yokoo et al., 2005; Yamagami et al., 2006). Such corneal endothelial cells would be bound with magnetic nanoparticles, for example 50 nm or 360 nm magnetic nanoparticles bought commercially or constructed using published methods (Schroder et al., 1986; Douglas et al., 1987; Sestier et al., 1998; Perrin et al., 1999; McCloskey et al., 2000; Tibbe et al., 2001). Binding of cells to coated nanoparticles would be based on specific antibody-antigen nanoparticle coatings, for example using antibodies against cadherin-11, integrin-beta-1, platelet-derived growth factor 1-alpha receptor, or neuropilin-1, all of which are expressed by corneal endothelial cells [our unpublished data]. Such magnetic nanoparticle-coated endothelial cells would be injected into the anterior chamber of the eye in a manner that can be done in a clinic, for example with a 30 gauge needle, without a requirement for incisional surgery. $10^3$-$10^6$ cells will be delivered by injection in a volume of 3-300 µL, but more typically around $10^4$-$10^5$ cells in a volume of 50-100 µL. A suitable magnet, for example a rare earth magnet of suitable strength, would be affixed in a patch to the surface of the eye external to the eyelid centered over the cornea. Over the course of a 1 hour to 7 days but more typically 16 hours to 3 days, the magnetic field would help affix the donor, nanoparticle-bound endothelial cells to the surface of the host/patient endothelial surface, after which time natural endothelial cell adhesion would take place, removing the need for additional magnetic field application. The external magnet would be removed. With time, the nanoparticles on the surface of the donor cells would degrade from the surfaces by natural proteolytic mechanisms, and be washed away in the fluid of the anterior chamber. Their small size would allow outflow through the trabecular meshwork and other natural outflow pathways without clogging these pathways or elevating intraocular pressure. The delivery of the magnetic endothelial cells to the internal corneal surface would allow improved pump function of the corneal endothelium and removal of fluid (edema) from the cornea. The cornea would subsequently become more clear, improving vision, and less edematous, decreasing the pain typically associated with this condition.

(b) Delivery of donor or autologous stem cells, photoreceptors, or retinal pigment epithelial (RPE) cells to the subretinal space in patients with photoreceptor/RPE dysfunction, as in age-related macular degeneration or retinitis pigmentosa. As in (a), such cells would be bound with magnetic nanoparticles, and injected subretinally, or perhaps through the bloodstream intravenously. Surgical implantation of a magnet or magnetic coil (electromagnet) would precede such injection, for example by affixing a rare-earth magnet by means of a sutured plate to the sclera behind the macula using a surgical technique in current use for the attachment of radioactive plaques in the treatment of ocular melanoma (Giblin et al., 1989; Shields et al., 1993; Shields et al., 1996; Shields et al., 1997). The magnetic field will cause localization and retention of the implanted cells at the site of degeneration, typically the macula. After healing and integration processes took hold, the magnet might be surgically removed. Alternatively the magnet could be left in place for future, additional cell treatments. The small, nano-scale, surface bound particles would as above degrade from the surfaces by natural proteolytic mechanisms allowing excretion from the eye. In this treatment paradigm, the delivery of magnetic cells to the posterior aspect of the retina would allow the improved function of the photoreceptors, enhancing visual acuity and visual field in these patients.

(c) Delivery of donor or autologous stem cells or retinal ganglion cells to the retinal surface, for such diseases as glaucoma or ischemic optic neuropathy, or other optic neuropathies. As in (b), such cells would be bound with magnetic nanoparticles, and injected intravitreally. Rather than simply floating around in the vitreous or sinking to the base of the eye, a posteriorly place magnet would pull the cells to the surface of the retina, perhaps over the macula, or in the retinal region of an acquired visual field deficit. Magnet and placement can be, for example as described in (b), above. Sequential localization of the magnetic field towards the head of the optic nerve could pull axons along their normal wiring pathways to the brain. As above, the small, nano-scale, surface bound particles would as above degrade from the surfaces by natural proteolytic mechanisms allowing excretion from the eye. In the treatment of glaucoma or other optic neuropathies with this version of the invention, the improved number of retinal ganglion cells, and the improved integration of these magnetic cells into the proper location of the eye, will allow for improved vision, and will contribute to the neuroprotection of the remaining retinal neurons preventing their cell death.

References, patents and other publications cited herein are hereby incorporated by reference.

REFERENCES

Chen K H, Azar D, Joyce N C (2001) Transplantation of adult human corneal endothelium ex vivo: a morphologic study. Cornea 20:731-737.

Douglas S J, Davis S S, Illium L (1987) Nanoparticles in drug delivery. Crit Rev Ther Drug Carrier Syst 3:233-261.

Giblin M E, Shields J A, Augsburger J J, Brady L W (1989) Episcleral plaque radiotherapy for uveal melanoma. Aust N Z J Opthalmol 17:153-156.

Goldberg J L, Klassen M P, Hua Y, Barres B A (2002a) Amacrine-signaled loss of intrinsic axon growth ability by retinal ganglion cells. Science 296:1860-1864.

Goldberg J L, Espinosa J S, Xu Y, Davidson N, Kovacs G T, Barres B A (2002b) Retinal ganglion cells do not extend axons by default: promotion by neurotrophic signaling and electrical activity. Neuron 33:689-702.

Joyce N C (2003) Proliferative capacity of the corneal endothelium. Prog Retin Eye Res 22:359-389.

Joyce N C, Zhu CC (2004) Human corneal endothelial cell proliferation: potential for use in regenerative medicine. Cornea 23:S8-S19.

Joyce N C, Meklir B, Neufeld A H (1990) In vitro pharmacologic separation of corneal endothelial migration and spreading responses. Invest Opthalmol Vis Sci 31:1816-1826.

Joyce N C, Meklir B, Joyce S J, Zieske J D (1996) Cell cycle protein expression and proliferative status in human corneal cells. Invest Opthalmol Vis Sci 37:645-655.

Lubbe A S, Alexiou C, Bergemann C (2001) Clinical applications of magnetic drug targeting. J Surg Res 95:200-206.

McCloskey K E, Chalmers J J, Zborowski M (2000) Magnetophoretic mobilities correlate to antibody binding capacities. Cytometry 40:307-315.

Meyer-Franke A, Kaplan M R, Pfrieger F W, Barres B A (1995) Characterization of the signaling interactions that promote the survival and growth of developing retinal ganglion cells in culture. Neuron 15:805-819.

Neuwelt E A, Weissleder R, Nilaver G, Kroll R A, Roman-Goldstein S, Szumowski J, Pagel M A, Jones R S, Remsen L G, McCormick C I, et al. (1994) Delivery of virus-sized iron oxide particles to rodent CNS neurons. Neurosurgery 34:777-784.

Perrin A, Theretz A, Lanet V, Vialle S, Mandrand B (1999) Immunomagnetic concentration of antigens and detection based on a scanning force microscopic immunoassay. J Immunol Methods 224:77-87.

Schroder U, Segren S, Gemmefors C, Hedlund G, Jansson B, Sjogren H O, Borrebaeck C A (1986) Magnetic carbohydrate nanoparticles for affinity cell separation. J Immunol Methods 93:45-53.

Schutt W, Gruttner C, Hafeli U, Zborowski M, Teller J, Putzar H, Schumichen C (1997) Applications of magnetic targeting in diagnosis and therapy—possibilities and limitations: a mini-review. Hybridoma 16:109-117.

Sestier C, Da-Silva M F, Sabolovic D, Roger J, Pons J N (1998) Surface modification of superparamagnetic nanoparticles (Ferrofluid) studied with particle electrophoresis: application to the specific targeting of cells. Electrophoresis 19:1220-1226.

Shields C L, Shields J A, De Potter P, Quaranta M, Freire J, Brady L W, Barrett J (1997) Plaque radiotherapy for the management of uveal metastasis. Arch Opthalmol 115: 203-209.

Shields J A, Shields C L, De Potter P, Singh AD (1996) Diagnosis and treatment of uveal melanoma. Semin Oncol 23:763-767.

Shields J A, Shields C L, De Potter P, Cu-Unjieng A, Hernandez C, Brady L W (1993) Plaque radiotherapy for uveal melanoma. Int Opthalmol Clin 33:129-135.

Tibbe A G, de Grooth B G, Greve J, Liberti P A, Dolan G J, Terstappen L W (2001) Cell analysis system based on immunomagnetic cell selection and alignment followed by immunofluorescent analysis using compact disk technologies. Cytometry 43:31-37.

Yamagami S, Mimura T, Yokoo S, Takato T, Amano S (2006) Isolation of human corneal endothelial cell precursors and construction of cell sheets by precursors. Cornea 25:S90-92.

Yokoo S, Yamagami S, Yanagi Y, Uchida S, Mimura T, Usui T, Amano S (2005) Human corneal endothelial cell precursors isolated by sphere-forming assay. Invest Opthalmol Vis Sci 46:1626-1631.

Zhu C, Joyce N C (2004) Proliferative response of corneal endothelial cells from young and older donors. Invest Opthalmol Vis Sci 45:1743-1751.

We claim:

1. A method of delivering a cell to a target tissue in an animal, said method comprising,
   (a) affixing, binding, or attaching at least one magnetic nanoparticle to the surface of said cell to obtain a magnetic particle-comprising cell, wherein the at least one magnetic nanoparticle is affixed to the cell surface by a cell-surface specific binding agent, by a covalent bond, or by a surface coating on the at least one magnetic nanoparticle comprising one or more antibodies, antibody fragments, proteins or sugar fragments that bind to said cells;
   (b) administering said magnetic particle-comprising cell to the target tissue of the animal;
   (c) applying a magnetic field to said target tissue such that said magnetic particle comprising cell is delivered to specific regions of said target tissue; and
   (d) maintaining said magnetic field over said target tissue to cause said cell to remain at the target tissue until the cell becomes affixed to the target tissue,
   wherein the cell is an ocular cell or optic nerve cell and the target tissue is eye tissue.

2. The method of claim 1, wherein the cell-surface specific binding agent comprises an antibody.

3. The method of claim 1 wherein the at least one magnetic nanoparticle has a mean diameter of no more than 500 nm.

4. The method of claim 3 wherein the at least one magnetic nanoparticle has a mean diameter of no more than 200 nm.

5. The method of claim 1 wherein the at least one magnetic nanoparticle comprises iron in any ferromagnetic form.

6. The method of any one of claims 1-5 wherein the at least one magnetic nanoparticle comprises said surface coating.

7. The method of any one of claims 1-5 wherein the magnetic particle-comprising cells are administered by injection or infusion or surface application.

8. The method of any one of claims 1-5 wherein the cell is selected from the group consisting of a corneal cell; a retinal cell; a retinal glial cell; a retinal endothelial cell or pericyte; and an optic nerve glial cell.

9. The method of any one of claims 1-5 wherein the animal is a mammal.

10. The method of claim 9 wherein the mammal is a human.

11. The method of claim 1, wherein the cell-surface specific binding agent is an antibody.

12. The method of claim 1, wherein said ocular cell is a corneal cell comprising an epithelial, stromal, or endothelial cell.

13. The method of claim 1, wherein said ocular cell is a retinal cell comprising a retinal ganglion cell, a photoreceptor or a retinal neuron.

14. The method of claim 1, wherein said ocular cell is a retinal glial cell comprising a retinal muller glial cell or retinal astrocyte.

15. The method of claim 1, wherein said optic nerve cell is an optic nerve glial cell comprising an astrocyte, oligodendrocyte, microglial cell, or one of their precursors.

\* \* \* \* \*